Aug. 28, 1945. A. F. ETTER Plant Pat. 659
APPLE TREE
Filed June 23, 1944
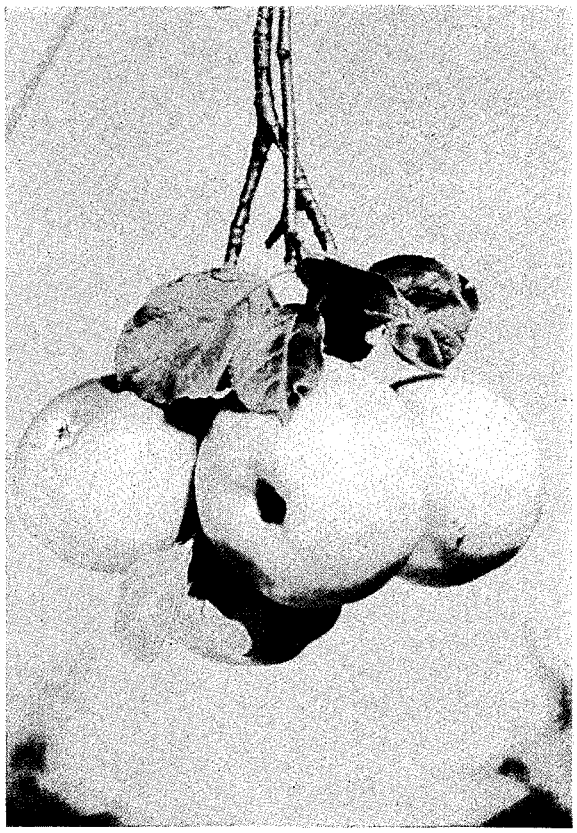
INVENTOR.
ALBERT F. ETTER.
BY
Chas. E. Townsend.
ATTORNEY.

Patented Aug. 28, 1945

Plant Pat. 659

UNITED STATES PATENT OFFICE

659

APPLE TREE

Albert F. Etter, Ettersburg, Calif., assignor to
George C. Roeding, Jr., Niles, Calif.

Application June 23, 1944, Serial No. 541,688

1 Claim. (Cl. 47—62)

This invention relates to a new variety of apple tree which has large, plentiful, golden fruit which begins to mature in October.

The apple tree is comparable with the Wagner but its fruit is more rounded out and of a deep golden color.

The accompanying colored photograph illustrates this new discovery.

The following is a detailed description of this new variety:

Size: The fruit is comparable in size to the Rhode Island Greening.
Shape: Extremely well filled out on both ends and often is slightly ribbed.
Stem: Medium slender.
Calyx: Tightly closed.
Basin: Shallow.
Skin: Very polished, clear golden yellow.
Calyx tube: Narrow.
Core: Very small indeed.
Seeds: Medium small, short, dark brown.
Flesh: Light to yellowish.
Foliage: Medium in size; healthy and abundant.
Origin: The apple tree originated by crossing a Wagner with Transcendent Crab and Field Cross.

The fruit is crisp and delightful to eat even when over-ripe; spritely, mild sub-acid flavor and firm flesh persist through cooking. The fruit is a good keeper, as the fruits may be stored for early winter desserts. The apple tree is productive and high in quality in a variety of climatic conditions.

What I claim is:

A new variety of apple tree characterized by fruit having a size comparable with the Rhode Island Greening, and a rounded shape, a polished, clear golden skin, small core, and light to yellowish flesh, substantially as herein disclosed.

ALBERT F. ETTER.